(12) United States Patent
Chen et al.

(10) Patent No.: US 9,119,843 B2
(45) Date of Patent: Sep. 1, 2015

(54) METHOD OF USING DOPAMINE REUPTAKE INHIBITORS AND THEIR ANALOGS FOR TREATING DIABETES SYMPTOMS AND DELAYING OR PREVENTING DIABETES-ASSOCIATED PATHOLOGIC CONDITIONS

(75) Inventors: Hao Chen, Columbia, MD (US); Ming Liu, Rockville, MD (US); Malathi Sathyamoorthy, Ellicott City, MD (US); Qi Su, Columbia, MD (US); Lisa Leary, Edgewater, MD (US); Wayne Shaobin Zhong, Gaithersburg, MD (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 0 days.

(21) Appl. No.: 13/509,881

(22) PCT Filed: Dec. 3, 2010

(86) PCT No.: PCT/US2010/058864
§ 371 (c)(1),
(2), (4) Date: Sep. 24, 2012

(87) PCT Pub. No.: WO2011/069051
PCT Pub. Date: Jun. 9, 2011

(65) Prior Publication Data
US 2013/0131127 A1    May 23, 2013

Related U.S. Application Data

(60) Provisional application No. 61/266,740, filed on Dec. 4, 2009.

(51) Int. Cl.
*A61K 31/4245* (2006.01)
*A61K 45/00* (2006.01)
*A61K 45/06* (2006.01)

(52) U.S. Cl.
CPC ............. *A61K 31/4245* (2013.01); *A61K 45/00* (2013.01); *A61K 45/06* (2013.01)

(58) Field of Classification Search
USPC ....................................................... 514/364
See application file for complete search history.

(56) References Cited

U.S. PATENT DOCUMENTS

| | | | |
|---|---|---|---|
| 3,277,108 A | 10/1966 | Daeniker | |
| 4,245,100 A | 1/1981 | Kholodov et al. | |
| 4,277,609 A | 7/1981 | Stein | |
| 4,301,285 A | 11/1981 | Stein | |
| 4,371,539 A | 2/1983 | Stein | |
| 4,371,697 A | 2/1983 | Stein | |
| 4,446,322 A | 5/1984 | Stein | |
| 5,554,626 A | 9/1996 | Moldt et al. | |
| 2004/0077679 A1 | 4/2004 | Cincotta | |
| 2005/0176680 A1 | 8/2005 | Lalji et al. | |
| 2007/0275907 A1 | 11/2007 | Chen et al. | |
| 2008/0260825 A1 | 10/2008 | Quik et al. | |
| 2009/0215839 A1 | 8/2009 | Chen et al. | |
| 2011/0288137 A1 | 11/2011 | Chen et al. | |
| 2012/0264698 A1 | 10/2012 | Chen et al. | |

FOREIGN PATENT DOCUMENTS

| | | |
|---|---|---|
| DE | 2028880 | 12/1971 |
| GB | 1262830 | 2/1972 |

OTHER PUBLICATIONS

R. Gainetdinov et al., "Glutamatergic modulation of hyperactivity in mice lacking the dopamine transporter", PNAS, 98(20): 11047-11054 (2001).
F. Hall et al., "Sex-dependent Modulation of Ethanol Consumption in Vesicular Monoamine Transporter 2 (VMAT2) and Dopamine Transporter (DAT) Knockout Mice", Neuropsychopharmacology, 28: 620-628 (2003).
Y. Mateo et al., "Role of serotonin in cocaine effects in mice with reduced dopamine transporter function", PNAS, 101 (1): 372-377 (2004).
S. Izenwasser et al., "Differential Relationships Among Dopamine Transporter Affinities and Stimulant Potencies of Various Uptake Inhibitors", Eur. J. Pharmacol., 263: 277-83 (2004).
P. Kunko et al., "Alterations in Locomotor Activity during Chronic Cocaine Administration: Effect on Dopamine Receptors and Interaction with Opioids", J. Pharmacol. and Exp. Ther, 285(1): 277-84 (1998).
G. Campiani et al., "Synthesis and Pharmacological Evaluation of Potent and Highly Selective D3 Receptor Ligands: Inhibition of Cocaine-Seeking Behavior and the Role of Dopamine D3/D2 Receptors", J. Med. Chem., 46: 3822-3839 (2003).
F. J. Garcia-Ladona et al., "BP 897, a Selective Dopamine D3 Receptor Ligand with Therapeutic Potential for the Treatemnt of Cocaine-Addiction", CNS Drug Reviews, 9: 141-158 (2003).
S. Schlussman et al., "Locomotion, stereotype, and dopamine D1 receptors after chronic "binge" cocaine in C57BL/6J and 129/J mice", Pharmacol. Biochem. Behav., 75: 123-131 (2003).
D. Platt et al., "Suppression of cocaine- and food-maintained behavior by the D2-like receptor partial agonist terguride in squirrel monkeys", Psychopharmacology, 166: 298-305 (2003).
S. Vorel, "Dopamine D3 Receptor Antagonism Inhibits Cocaine-Seeking and Cocaine-Enhanced Brain Reward in Rats", J. Neurosci., 22(21): 9595-9603 (2002).
E. Ellinwood et al., "Effect of daily dosing duration of direct and indirect dopamine receptor agonists: cocaine cross-tolerance following chronic regimens", Eur. Neuropsychopharmacol., 12: 407-15 (2002).
J. Owens et al., "Second generation SSRIS: human monoamine transporter binding profile of escitalopram and R-fluoxetine", Encephale, 28(4): 350-5 (2002).
A. Zhang et al., "Further Studies on Conformationally Constrained Tricyclic Tropane Analogues and Their Uptake Inhibition at Monoamine Transporter Sites: Synthesis of (Z)-9-(Substituted arylmethylene)-7-azatricyclo[4.3.1.0] decanes as a Novel Class of Serotonin Transporter Inhibitors", J. Med. Chem., 45: 1930-1941 (2002).

(Continued)

*Primary Examiner* — Kathrien Cruz
(74) *Attorney, Agent, or Firm* — Thomas H. Walls; Dann, Dorfman, Herrell and Skillman, P.C.

(57) ABSTRACT

Method of using dopamine reuptake inhibitors, e.g., sydnonimine derivatives, for the management of diabetic symptoms and associated complications or conditions, such as hyperglycemia and diabetic neuropathy.

8 Claims, 2 Drawing Sheets

(56) References Cited

OTHER PUBLICATIONS

C. Sanchez eta l., "Escitalopram, the S-(+)enantionmer of citalopram, is a selective serotonin reuptake inhibitor with potent effects in animal models predictive of antidepressant and anxiolytic activities", Psychopharmacology, 167: 353-362 (2003).
E. Fish et al., "Anxiolytic-Like Effects of Escitalopram, Citalopram, and R-Citalopram in Maternally Separated Mouse Pups", J. Pharmacol. Exp. Ther., 308: 474-80 (2004).
N. Volkow et al., "Therapeutic Doses of Oral Methylphenidate Significantly Increase Extracellular Dopamine in the Human Brain", J. Neurosci., 21(2) RC 121 (2001).
P. D'Aquila et al., "The role of dopamine in the mechanism of action of antidepressant drugs", Eur. J. Pharmacol., 405: 365-373 (2000).
I. Sora et al., "Molecular mechanisms of cocaine reward: Combined dopamine and serotonin transporter knockouts eliminate cocaine place preference", PNAS, 98(9): 5300-5305 (2001).
J. Witkin et al., "Behavorial, Toxic, and Neurochemical Effects of Sydnocarb, a Novel Psychomotor Stimulant: Comparisons with Methamphetamine", J. Pharmacol. Exp. Ther., 288(3): 1298-1310 (1999).
I.S. I S Slyusarenko et al., "Sydnonimines prepared from E-aminocaproic acid", Khimiya Geterotsiklicheskikh Soedinenii, 11: 1469-72 (1973) CAPLUS record.
S. Erdo et al., Inhibition of Dopamine Uptake by a New Psychostimulant Mesocarb (Sydnocarb), Polish Journal of Pharmacology and Pharmacy, 33: 141-147 (1981), Abstract.
M. Thorpy, "Therapeutic advances in narcolepsy", Sleep Medicine, 8: 427-440 (2007).
L. E. Kholodov et al., "Sydnones and sydnonimines. XXXV. Salts and exocyclic derivatives of some sydnonimines", Zhurnal Organicheskoi Khimii, 3(8): 1513-1518 (1967) (CAPLUS record).
H. Takahashi et al., "The Role of Extrastriatal Dopamine D2 Receptors in Schizophrenia", Biol. Psychiatry, 59: 919-928 (2006).
L. E. Kholodov et al., "Synthesis and pharmacological activity of some 3-substituted sydnone imines", Khimiko-Farmatsevticheskii Zhurnal, 2(5): 3-7 (1968).
Z.A. Olovyanishnikova et al., "Electrophilic substitution in N-exocarbamoyl derivatives of sydnone imines", Khimiya Geterotsiklicheskikh Soedinenii, 9: 1198-203 (1975) (CAPLUS record).
Z.A. Olovyanishnikova et al., "Phenylethyl derivatives of sydnonimines", Khimiko-Farmatsevticheskii Zhurnal, 6(6): 20-3 (1972).
Al'tshuler et al., Farmakologiya/Toksikologiya, 43: 153-158 (1980).
Definition for "acyl", Hawley's Condensed Chemical Dictionary, 14th edition (2002).
S. Izenwasser et al., "Differential relationships among dopamine transporter affinities and stimulant potencies of various uptake inhibitors", Eur. J. Pharmacol., 263: 277-283 (1994).
V.A. Krasov et al., "Sidnocarb Treatment of Young Schoolchildren with Hyperdynamic Syndrome", Zhurnal Nevropatologii I Psikhiatrii Imeni S.S. Korsakova, 88(8): 97-101 (1988).
English translation of Krasov et al., Zhurnal Nevropatologii/ Psikhiatrii Imeni S.S. Korsakova, 88(8): 97-101 (1988).
English translation of Al'tshuler et al., Farmakologiya/ Toksikologiya, 43: 153-158 (1980).
F. George, "Cocaine produces low dose locomotor depressant effects in mice", Psychopharmacology, 99: 147-150 (1989).
S.H. Heil et al., "Comparison of the subjective, physiological, and psychomotor effects of atomoxetine and methylphenidate in light drug users", Drug and Alcohol Dependence, 67: 149-156 (2002).
H. Mitchell et al., "The Effects of Norepinephrine Transporter Inactivation on Locomotor Activity in Mice", Biol. Psychiatry, 60: 1046-1052 (2006).
K. Blum et al., "Attention-deficity-hyperactivity disorder and reward deficiency syndrome", Neuropsychiatric Disease and Treatment, 4(5): 893-917 (2008).
B. Campbell et al., "Obesity, Attention Deficit-Hyperactivity Disorder and the Dopaminergic Reward System", Coll. Antropol., 31: 33-38 (2007).
M. Gallego et al., "Diabetes-Induced Biochemical Changes in Central and Peripheral Catecholaminergic Systems", Physiol. Res., 52: 735-741 (2003).
J. Morrison et al., "Sensory and autonomic nerve changes in the monosodium glutamate-treated rat: a model of type II diabetes", Exp. Physiol., 93: 213-222 (2007).
R. Ramakrishnan et al., "A short-term diabetes induced changes of catecholamines and p38-MAPK in discrete areas of rat brain", Life Sciences, 77: 1825-1835 (2005).
V. Russell et al., "Response variability in Attention-Deficity/Hyperactivity Disorder: a neuronal and glial energetics hypothesis", Behavorial and Brain Functions, 2: 30 (2006).
English translation of Temkov et al., "Study of a New Psychostimulant Sydnocarb", Nuerology, Psychiatry and Neurosurgery, 14: 179-183 (1975) (translated Oct. 2010).
Temkov et al., Nevrologiya, Psikhiatriya/Nevrokhirurgiya, 14: 179-183 (1975).
Center for Cognitive-Development Assessment & Remediation definition for "hyperdynamic syndrome" (http://www.bgcenter.com/bgqa/medical9.htm), accessed Oct. 14, 2010.
National Institute of Mental Health, Attention Deficit Hyperactivity Disorder, http://www.nimh.nih.gov/health/publications/attention-deficit-hyperactivity-disorder/complete-index.shtml, 2008.
Assimacopoulos-Jeannet, Francoise D. et al., "Studies on α-Adrenergic Activation of Hepatic Glucose Output. Studies on Role of Calcium in alpha-Adrenergic Activation of Phosphorylase", J. Biol. Chem., 252(8): 2662-2669 (1977).
Prabhuswamy, Mukesh et al., "Letter to the Editor. Methylphenidate and Hypertension", Journal of Child and Adolescent Psychopharmacology, 16(6): 805-806 (2006).
Esler, Murray et al., "The Sympathetic Neurobiology of Essential Hypertension: Disparate Influences of Obesity, Stress, and Noradrenaline Transporter Dysfunction?", AJH, 14: 139S-146S (2001).
Assimacopoulos-Jeannet, Francoise D. et al., "Studies on α-Adrenergic Activation of Hepatic Glucose Output. Studies on Role of Calcium in α-Adrenergic Activation of Phosphorylase", J. Biol. Chem., 252(8): 2662-2669 (1977).
Blackmore, Peter F. et al., "Studies on α-Adrenergic Activation of Hepatic Glucose Output. The Role of Mitochondrial Calcium Release in α-Adrenergic Activation of Phosphorylase in Perfused Rat Liver", J. Biol. Chem., 254(15): 6945-6950 (1979).
Cabassi, Aderville et al., "Norepinephrine Reuptake is Impaired in Skeletal Muscle of Hypertensive Rats in Vivo", Hypertension, 37: 698-702 (2001).
Brealey, David et al., "Hyperglycemia in Critical Illness: A Review", J. Diabetes and Sci. Technol., 3(6): 1250-1260 (2009).
Schlaich, Markus P. et al., "Sympathetic Augmentation in Hypertension. Role of Nerve Firing, Norepinephrine Reuptake, and Angiotensin Neuromodulation", Hypertension, 43: 169-175 (2004).
Studer, Rebecca K. et al., "Regulation of Hepatic Glycogenolysis by Glucoagon in Male and Female Rats. Role of cAMP and Ca2+ and Interactions Between Epinephrine and Glucagon", J. Biol. Chem., 259(6): 3596-3604 (1984).

METHOD OF USING DOPAMINE REUPTAKE INHIBITORS AND THEIR ANALOGS FOR TREATING DIABETES SYMPTOMS AND DELAYING OR PREVENTING DIABETES-ASSOCIATED PATHOLOGIC CONDITIONS

CROSS-REFERENCE TO RELATED APPLICATIONS

The present application is the U.S. National Stage of International Application No. PCT/US2010/058864, filed Dec. 3, 2010, which claims the benefit of U.S. Provisional Patent Applications No. 61/266,740, filed Dec. 4, 2009, the entire disclosure of each of the aforesaid applications being incorporated by reference herein.

FIELD OF INVENTION

The present invention relates to the field of pharmacological management of diabetes and various associated disease manifestations. More specifically, the present invention provides a method of using dopamine reuptake inhibitors, including certain sydnonimine derivatives, for the management of diabetic symptoms and associated complications or conditions, such as hyperglycemia and diabetic neuropathy.

BACKGROUND OF THE INVENTION

Diabetes is a modern epidemic affecting an increasingly large number of populations from industrial countries to the developing world. The cost of managing diabetes in the United States alone is about $174 billion, $116 billion of which are directed towards medical care.

The hallmark symptom of diabetes mellitus is hyperglycemia, i.e. high levels of blood glucose (also known as blood sugar). Such conditions are primarily the result of insufficient insulin production (Type I diabetes) or from defects in response to insulin action (Type II diabetes). A chronic diabetic condition causes serious complications or co-morbidities, such as heart disease, stroke, impaired renal function, or nephropathy, high blood pressure, both central and peripheral nerve damage or neuropathy, cataracts and/or blindness and amputations.

According to the National Diabetes Information Clearinghouse (NDIC) report (a service provided by National Institute of Diabetes and Digestive and Kidney Diseases, NIDDK, NIH), in the United States, in 2007 there were 23.6 million (approximately 7.8 percent of the population) diabetic patients along with 1.6 million new cases of diabetes diagnosed in the same year. About half (12.1 million) of the diabetic population is age 60 or older. Moreover, an estimated 57 million American adults exhibit pre-diabetic conditions (e.g. persistent hyperglycemic conditions) in 2007, a warning sign of potential outbreak.

The etiology of diabetes is still under investigation. The primary focus of diabetic management is the reduction of blood glucose levels. Few therapeutic initiatives with regard to diabetic management started with a neurological approach. Mediating and attenuating diabetic neurological symptoms are often afterthoughts.

Diabetic conditions are often linked with altered central and sympathetic nervous systems. Most chronic diabetic patients eventually develop neuropathy of different clinical manifestations. According to a statement made by the American Diabetes Association, the most common among the neuropathies are chronic sensorimotor distal symmetric polyneuropathy (DPN) and the autonomic neuropathies. Up to 50% of DPN may be asymptomatic but the patient is at risk of insensate injury to their feet and >80% of amputations follow a foot ulcer or injury. Additionally, such neuropathy also includes autonomic manifestations of every system in the body, which causes substantial morbidity and increased mortality, particularly when cardiovascular autonomic neuropathy (CAN) is present. Glucose and/or insulin are not known to directly mediate sensory or nociceptive perceptions such as hypoalgesia or hyperalgesia (different neuropathic manifestations), nor are they known to be linked with cardiovascular autonomic regulations. Literature reports indicate that strict glycemic control may mediate neuropathies, but not eliminate the symptoms entirely. These indications point to other neurological mediators that 1) contribute to the regulation of glucose/energy homeostasis and 2) are dis-regulated under pre-diabetic or diabetic conditions (genetic and/or environmental factors).

Epidemiological studies have linked child-hood obesity and diabetes with neurological dysfunctions like attention deficit hyperactive disorder (ADHD). These studies suggest that dopaminergic transmission that evolved to increase cognition is also coupled with attention and energy management (Campbell and Eisenberg, 2007). One of the working hypotheses regarding ADHD etiology is that patients have handicapped energetic management between neuronal and glial cells (Russell, et al 2006). Besides ADHD, there is a substantial body of clinical evidence and research reports linking anxiety, stress and depression with diabetes. These mechanisms are still to be explored and understood. Nevertheless, the response of neuroendocrine, hypothalamic-pituitary-adrenal axis and sympathetic nervous system, to stressors may be key contributing factors to the underlying etiology. Based on these studies, a panel of experts has suggested that activation of the dopaminergic circuitry may be a viable and effective clinical management paradigm (Blum et al, 2008).

Diabetes alters the central and sympathetic nervous systems that may lead to behavior manifestations. Stress and depression, central nervous system conditions, may cause metabolic changes leading to diabetes. These disease symptoms may share common roots. To further support the role of neuronendocrine system in diabetes, especially with regards to the role of dopaminergic function, there is a substantial body of supporting evidence from animal studies When treated neonatally with monosodium glutamate, Wistar rats develop symptoms of Type II diabetes, i.e. hyperglycemia, glucose intolerance, beta-cell morphological changes, and sensory and autonomic nerve changes including the development of a hypoalgesic state. Concomitantly, there are noted changes in catecholamine synthesis in different peripheral tissues and sympathetic nerves (Morrison et al, 2007).

In one animal model of Type I diabetes (Sprague-Dawley rats treated with Streptozotocin), a brief episode of the chemically induced diabetes brought changes in dopaminergic neurotransmission by reducing levels of dopamine in a tissue specific manner. Notably, in the peripheral (sympathetic) nervous system, dopamine content remains unperturbed at adrenal glands, blood serum and cardiac ventricles; yet there is a 14 to 15 fold reduction of dopamine in the stellate ganglion (physiologically, the human stellate ganglion, or cervicothoracic ganglion, may be blocked for different medical conditions; reduction of catecholamine may be an indication of the reduction of catecholamine neurotransmission in the sympathetic nerves system leading to conditions such as DPN). In the central nervous system, dopamine levels remain unchanged at medulla and pons; however, there is a 4-fold reduction in the midbrain and a 5-fold reduction in the striatum (a underlying biochemical mechanism of neurological manifestations and symptoms, such as ADD, depression, anxiety and Parkinson's disease). Changes in other catecholamines, e.g. norepinephrine and epinephrine, are noted but less significant (Gallego et al, 2003). In another study, besides similar observations in altering catecholamine levels in different brain regions, short term diabetes also altered the expression levels of signal transduction proteins such as CaMKII, PKC-alpha, and p38-MAPK kinases, indicating the impact of diabetes at the neuronal level (Ramakrishnan et al, 2005) and changes in cellular signal transductions.

Human epidemiological studies have shown that when humans are on a limited caloric diet, there are fewer incidences of diabetes, as well as cancer, obesity, anxiety, depression and many other disease states and conditions. When the BL/6 is on a healthy and constant caloric restriction diet (recapitulating human condition), the animal subjects show less anxiety and less depressive behavior; that is the caloric-restricted (CR) subjects spend more time in the center of the open field study; more time in the open arm of the elevated plus maze study, and less time immobilized in the forced swim test (as compared with binge fed and normal control models). Dopaminergic and alpha-adrenergic signal transduction are amongst the top up-regulated genes (potentially indicating the underlying mechanism between ADHD and diabetes) in these CR subjects. And the western blot analysis indicated a specific activation of dopaminergic activities (e.g. up-regulation of cAMP-regulated phosphoprotein, a protein specifically associated with dopaminergic neurotransmissions).

From the above discussions, it may be concluded that 1) the diabetic condition appears to negatively impact the catecholaminergic, especially dopaminergic systems leading to conditions of neuropathology; and/or 2) neuropathological conditions may negatively impact the "insulinergic" system, thus supporting the diabetic condition. There is increasing evidence in the literature indicating the importance of insulin in neurological functions, including age-related neurodegenerative conditions such as Alzheimer's disease.

There is currently no cure for either Type I or Type II diabetes. Life style changes, e.g. changing diet and increasing exercise, may mediate aspects of disease-related conditions, but such changes and alternatives are often neither feasible nor effectively adopted, especially in aging populations. Pharmacological management is the primary means to control the development of diabetic complications.

For Type I diabetes, the management has been with insulin. Pharmacological intervention of Type II diabetes has been attempted with blood glucose control using medications such as Metformin (glucophage) or Glibenclamide (glyburide). Metformin inhibits the release of glucose from liver glycogen; Glibenclamide (and other sulfonylureas), inhibits pancreatic beta-cell potassium channels, and thus stimulates insulin secretion. Although these drugs are mostly safe, they cannot be used in patients with compromised hepatic functions. There are other drugs that mediate the diabetic condition by alternative biochemical mechanisms, e.g. stimulating insulin secretion (e.g. repaglinide), inhibiting glucose metabolism (e.g. glucosidase inhibitor, acarbose), mediating gastric emptying (e.g. pramlintide), etc. The most recent diabetic medications are agonists of glucagon-like peptide-1 of the incretin hormone receptor (GLP-1 agonist) and dipeptidyl-peptidase-4 inhibitors (e.g. sitagliptin). A common complication of most of these drugs is hypoglycemia, a condition often resulting in seizures, unconsciousness and occasionally permanent brain damage or death. Ideally, a pharmacological agent capable of maintaining glucose homeostasis at a healthy level without such complications would improve the current diabetes treatment paradigm.

The human clinical evidence, human epidemiological and animal model studies referred to above support the concept that activation of the dopaminergic circuitry may be a viable and effective clinical management approach for both Type I and Type II diabetes.

SUMMARY OF THE INVENTION

To address the need of developing more effective ways of treating diabetic symptoms and managing conditions associated with diabetes, and diabetic neuropathy in particular, the present invention provides a method employing one or more dopamine reuptake inhibitors that may be used for the treatment of diabetic symptoms and/or prophylaxis of diabetes-associated pathologic conditions.

Such dopamine reuptake inhibitors may be administered individually, or in combination, as well as in a combination including at least one other active agent that is effective in diabetes management.

Based on studies conducted to date by the present inventors, it appears that the method of the invention may be effective to attenuate diabetic neurological manifestations such as neuropathic pain, sensorimotor distal symmetric polyneuropathy and autonomic neuropathy. As a result, the method of the invention may also be effective for restoring sensation in lower extremities.

Thus, the present invention offers a holistic approach to diabetes management by supplementing glycemic control with mediating and attenuating neurological symptoms using the methods described herein. As will appear below, this improved treatment modality is based on a greater understanding of related patho-biochemical mechanisms, including neurobiology, provided by the present inventors.

DETAILED DESCRIPTION OF THE INVENTION

Among the dopamine reuptake inhibitors that may be used in practicing this invention are compounds of the formula:

(I)

wherein $R_1$, $R_2$, $R_3$, $R_4$, $R_5$ and $R_6$, independently of one another, are substituents selected from H, $C_1$-$C_6$ alkyl, OH, halogen, $C_5$-$C_{14}$ aryl, $C_6$-$C_{20}$ aralkyl, $C_1$-$C_6$ alkylthio, $C_1$-$C_6$ alkoxy, SH, $C_2$-$C_6$ alkenyl, $C_2$-$C_6$ alkynyl, $C_3$-$C_6$ cycloalkyl, CN, $NO_2$, carboxy, carbalkoxy, carboxamido, alkylsulfonyl, alkylsulfonyloxy, aminosulfinyl, monoalkylaminosulfinyl, dialkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkyaminosulfonylalkyl, aminosulfinylalkyl, monoalkylaminosulfinylalkyl, dialkylaminosulfinylalkyl, said alkyl, alkenyl, alkynyl or cycloalkyl substituent being optionally substituted by at least one halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy group, said aryl and aralkyl substituent being optionally substituted by at least one halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy group;

$R_a$, $R_b$ and $R_c$, independently of one another, represent substituents selected from H, $C_1$-$C_4$ alkyl, phenyl or phenyl $C_1$-$C_4$ alkyl, said alkyl substituent, said phenyl substituent and said phenyl $C_1$-$C_4$ alkyl substituent being optionally substituted by at least one halogen, OH, SH, $NH_2$, $C_1$-$C_4$ methylalkylamino, $C_1$-$C_4$ dialkylamino, COOH, CN, $NO_2$, $C_1$-$C_4$ alkyl or $C_1$-$C_4$ alkoxy group;

m, n and k are independent integers from 0-4, except that m+n≠0;

and the pharmaceutically acceptable salts of said compound.

It should be appreciated that compounds of Formula (I), above, may have one or more asymmetric centers and thus exist as stereoisomers, including enantiomers and diastereomers, which are usually named according to the Cahn-Ingold-Prelog system. Although the structure of Formula I is represented without regard to stereochemistry, it is intended to include all possible stereoisomers, which may be racemic mixtures or other mixtures of R and S stereoisomers (scalemic mixtures which are mixtures of unequal amounts of enantiomers), as well as resolved, substantially pure optically active forms, and pharmaceutically acceptable salts thereof.

Stereoisomers of the compounds of Formula (I), above, can be selectively synthesized or separated into pure, optically-active form using conventional procedures known to those skilled in the art of organic synthesis. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

All of the various isomeric forms of the compound of Formula (I), above, are within the scope of this invention.

As used herein, the "alkyl" refers to saturated straight and branched chain hydrocarbon radicals, having 1-6 and preferably 1-4 carbon atoms. The term "alkenyl" is used to refer to unsaturated straight and branched chain hydrocarbon radicals including at least one double bond, and having 2-7 and preferably 2-5 carbon atoms. Such alkenyl radicals may be in trans (E) or cis (Z) structural configurations. The term "alkynyl" is used herein to refer to both straight and branched unsaturated hydrocarbon radicals including at least one triple bond and having 2-7 and preferably 2-5 carbon atoms.

The term "cycloalkyl" as used herein refers to a saturated cyclic hydrocarbon radical with one or more rings, having 3-14 and preferably 5 or 6-10 carbon ring-atoms.

Any alkyl, alkenyl, alkynyl or cycloalkyl moiety of a compound described herein may be substituted with one or more groups, such as halogen, OH, SH, $NH_2$, C1-C4 monoalkylamino, C1-C4 dialkylamino, COOH, CN, NO2, C1-C4 alkyl or C1-C4 alkoxy.

The term "aryl" as used herein refers to an aromatic hydrocarbon radical composed of one or more rings and having 5 or 6-14 carbon atoms and preferably 5 or 6-10 carbon atoms, such as phenyl, naphtnyl, biphenyl, fluorenyl, indanyl, or the like. Any aryl moiety of a compound described herein may be substituted with one or more groups, such as halogen, OH, SH, $NH_2$, C1-C4 monoalkylamino, C1-C4 dialkylamino, COOH, CN, NO2, C1-C4 alkyl or C1-C4 alkoxy. The aryl moiety is preferably substituted or unsubstituted phenyl.

The term "arylalkyl" or "aralkyl" as used herein refers to radicals having 6 to 20 carbon atoms that combine both an aryl and an alkyl group, as defined above. Any aralkyl moiety of a compound described herein may optionally be substituted with one or more of the same substituent groups mentioned above in reference to the aryl radical.

The term "halogen" or "halo" as used herein refers to Fl, Cl, Br and I.

The term "alkoxy" refers to alkyl-O—, in which alkyl is as defined above.

The term "alkylthio" refers to alkyl-S—, in which alkyl is as defined above.

The term "carboxy" refers to the moiety —C(=O)OH.

The term "carbalkoxy" refers to the moiety —C(=O)O-alkyl, in which alkyl is as defined above.

The term "carboxamido" refers to the moiety —C(=O)O—NR'R", in which R' and R", each independently represents H, alkyl, aryl or aralkyl, all as previously defined.

The term "alkylsulfonyl" refers to the moiety —S(=O)$_2$-alkyl, in which alkyl is as previously defined.

The term "alkylsulfonyloxy" refers to the moiety —OS(=O)$_2$-alkyl, wherein alkyl is as previously defined.

The term "amino(monoalkylamino-, dialkylamino-)sulfinyl" refers to the moiety —S(=O)NR'R" in which R' and R" each independently represents H, alkyl, aryl or aralkyl, all as previously defined.

The term "amino(monoalkylamino-, dialkylamino-)sulfonyl" refers to the moiety —S(=O)$_2$NR'R", in which R' and R" each independently represents H, alkyl, aryl or aralkyl, all as previously defined.

The term "alkylsulfonylamino" refers to the moiety —NHS(=O)$_2$-alkyl, in which alkyl is as previously defined.

The term "hydroxysulfonyloxy" refers to the moiety —OS(=O)$_2$OH. The term "alkoyxsulfonyloxy" refers to the moiety —OS(=O)$_2$O-alkyl, in which alkyl is as previously defined.

The term "alkylsulfonyloxy" refers to the moiety —OS(=O)$_2$-alkyl, in which alkyl is as previously defined.

The term "hydroxysulfonyl" refers to the moiety —S(=O)$_2$OH.

The term "alkoxysulfonyl" refers to the moiety —S(=O)$_2$O-alkyl, wherein alkyl is as previously defined.

The term "alkylsulfonylalkyl" refers to the moiety -alkyl-S(=O)$_2$-alkyl, wherein alkyl (each instance) is as previously defined.

The term "amino(monoalkylamino-, dialkylamino-)sulfonylalkyl" refers to the moieties -alkyl-S(=O)$_2$—NR'R", wherein alkyl is as previously defined, and R' and R" each independently represents H, alkyl, aryl or aralkyl, all as previously defined.

The term "amino(monoalkylamino-, dialkylamino-)sulfinylalkyl" refer to the moieties -alkyl-S(=O)—NR'R", wherein alkyl is as previously defined, and R' and R" each independently represents H, alkyl, aryl or aralkyl, all as previously defined.

Preferred are the compounds of Formula (I), above, wherein phenyl rings A and/or B are mono- or di-substituted. When the A and/or B ring is mono-substituted, para-substitution is preferred. When the A and/or B ring is di-substituted, 3,4 di-substitution is preferred. Most preferred are compounds in which the A ring is para-substituted, e.g., 3-(p-methylbenzyl)sydnominine-N-phenylcarbamoyl, compounds in which the B ring is 3,4-di-substituted, e.g., 3-phenethyl-sydnominine-N-(3',4'-dichlorophenyl)carbamoyl and compounds in which the A ring is para-substituted and the B ring is 3,4-di-substituted, e.g., 3-(p-nitrophenethyl)-sydnominine-N-(3',4'-dinitro-phenyl)carbamoyl. Also preferred are compounds wherein m+n=1 or 3 in formula (I), above.

The term "pharmaceutically acceptable salts" as used herein refers to salts derived from non-toxic physiologically compatible acids and bases, which may be either inorganic or organic. Thus, when a compound of Formula I has an acid moiety, e.g., 3-(p-carboxybenzyl), sydnominine-N-phenylcarbamoyl, useful salts may be formed from physiologically compatible organic and inorganic bases, including, without limitation, alkali and alkaline earth metal salts, e.g., Na, Li, K, Ca, Mg, as well as ammonium salts, and salts of organic amines, e.g., ammonium, trimethylammonium, diethylammonium, and tris-(hydroxymethyl)methylammonium salts. The compounds of the invention also form salts with organic and inorganic acids, including, without limitation, acetic, ascorbic, lactic, citric, tartaric, succinic, fumaric, maleic, malonic, mandelic, malic, phthalic, salicyclic, hydrochloric, hydrobromic, phosphoric, nitric, sulfuric, methane sulfonic, naphthalene sulfonic, benzene sulfonic, toluene sulfonic and similar known, physiologically compatible acids. In addition, when a compound of Formula I contains both a basic moiety and an acidic moiety, zwitterions ("inner salts") may be formed and are included within the term "salt(s)" as used herein.

In general, the compounds of the invention can be administered to achieve specific dopamine reuptake inhibition by using any acceptable means known in the art, either alone or in combination with one or more other therapeutic agents. Thus, the active agent(s) can be administered orally, parenterally, such as by intravenous or intraarterial infusion, intramuscular, intraperitoneal, intrathecal or subcutaneous injection, by liposome-mediated delivery, rectally, vaginally, by inhalation or insufflation, transdermally or by otic delivery.

The method of treating diabetic symptoms and delaying or preventing diabetes-associated pathologic conditions described herein may be used as an adjunct to the current standard of care for both Type I and Type II diabetes. To that end, one or more of the dopamine reuptake inhibitors described herein may be coadministered with insulin, for the treatment of Type I diabetes, or with any of the numerous agents administered for the treatment of Type II diabetes. The latter include, without limitation, glucophage, glyburide, repaglinide, acarbose, pramlintide and sitagliptin. These agents may be administered as separate dosage units or formulated for administration together, according to procedures well known to those skilled in the art. See, for example, Remington: The Science and Practice of Pharmacy, 20$^{th}$ ed., A. Genaro et al., Lippencot, Williams & Wilkins, Baltimore, Md. (2000).

The dopamine reuptake inhibitors described above may be administered singly or together, as well as in combination (singly or together) with at least one dopamine receptor agonist. The dopamine receptor agonists that may be used in accordance with the present invention includes, without limitation, cabergoline, pergolide, pramipexole, ropinirole, apomorphine, rotigotine, fenoldopam, dopamine, and levodopa. These are clinically effective dopamine receptor agonists, which should be administered in accordance with the manufacturers' recommendations.

The dopamine reuptake inhibitors described above may be administered singly or together, as well as in combination (singly or together) with at least one of a monoamine oxidase inhibitor (MAOI) and a catecholamine o-methyl transferase inhibitor (COMTI).

A MAOI, when used in the practice of this invention, has the effect of promoting dopaminergic functions by inhibiting dopamine metabolism, thus extending and expand the duration and functional domain of dopaminergic activities.

Suitable MAOIs include, without limitation, Harmine, Harmaline, Tetrahydroharmine, Harmalol, Benmoxin (Nerusil, Neuralex), Hydralazine (Apresoline) Hydrazine, Iproclozide (Sursum), Iproniazid (Marsilid, Iprozid, Iprozid, Rivivol, Propilniazida), Isocarboxazid (Marplan), Mebanazine (Actomol), Metfendrazine (H.M.-11), Monomethylhydrazine, Nialamide (Niamid), Phenelzine (Nardil), Pheniprazine (Caton), Phenoxypropazine (Drazine), Phenylhydrazine Pivalylbenzhydrazine (Tersavid, Neomarsilid), Safrazine (Safra), Non-hydrazines, Tranylcypromine (Parnate), Befloxatone, Brofaromine (Consonar), Cimoxatone, Clorgyline, Curcumin, Isoniazid, Minaprine (Cantor), Moclobemide (Aurorix, Manerix), Pirlindole (Pirazidol), Toloxatone (Humoryl), Tyrima (CX157), Catechin Desmethoxyyangonin, Epicatechin, Lazabemide, Pargyline (Eutonyl), Piperine, Rasagiline (Azilect), Selegiline.

COMTI may be used in carrying out the method of the invention, in order to inhibit dopamine metabolism, thus extending and expanding the duration and functional domain of dopaminergic activities.

Suitable COMTI for this purpose include, without limitation, tolcapone and entacapone.

The above-described MAOI and COMTI are clinically useful therapeutic agents which should be administered in accordance with the manufacturers' recommendation.

Each of the aforementioned therapeutic agents, i.e., dopamine reuptake inhibitor(s), MAOI(s) and COMTI(s) may be co-administered in the form of discrete dosage units, or formulated for administration together, using procedures described in Remington: The Science and Practice of Pharmacy, supra.

Normally, a daily dose of the compound of the invention in the range from about 0.01 mg to about 200 mg/kg of body weight can be administered. A daily dose of from 0.1 to 100, and preferably from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

As used herein, the expression "a method for treatment of diabetic symptoms" refers to a treatment using one or more of the dopamine reuptake inhibitors described herein, with or without the aforementioned MAOIs and COMTIs, which provide relief or alleviation of the clinically recognized symptoms of diabetes including, without limitation, hyperglycemia. The methods described herein may also be used to delay the onset or prevent the occurrence of diabetes-associated pathologic conditions. The more common types of diabetic complications are diabetic sensory neuropathy, diabetic autonomic neuropathy, diabetic nephropathy, diabetic retinopathy, and diabetic angiopathy.

The compounds of the invention will typically be administered from 1-4 times a day, so as to deliver the above-mentioned daily dosage. However, the exact regimen for administration of the compounds and compositions described herein will necessarily be dependent on the needs of the individual subject being treated, the type of treatment administered and the judgment of the attending medical specialist. As used herein, the term "subject" includes both humans and animals.

The compounds of the invention may be administered as such, or in a form from which the active agent can be derived, such as a prodrug. A prodrug is a derivative of a compound described herein, the pharmacologic action of which results from the conversion by chemical or metabolic processes in vivo to the active compound. Prodrugs include, without limitation, ester derivatives of the compounds of formula I, above. Other prodrugs may be prepared according to procedures well known in the field of medicinal chemistry and pharmaceutical formulation science. See, e.g., Lombaert et al., J. Med. Chem., 37: 498-511 (1994); and Vepsalainen, Tet. Letters, 40: 8491-8493 (1999).

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agent may also be incorporated into a conventional transdermal delivery system.

As used herein, the expression "pharmaceutically acceptable carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20$^{th}$ edition, A. R. Genaro et al., Part 5, Pharmaceutical Manufacturing, pp. 669-1015 (Lippincott Williams & Wilkins, Baltimore, MD/Philadelphia, Pa.) (2000)) discloses various carriers used in formulating pharmaceutical compositions and known techniques for the preparation thereof. Except insofar as any conventional pharmaceutical carrier medium is incompatible with the compounds of the present invention, such as by producing an undesirable biological effect or otherwise interacting in an deleterious manner with any other component(s) of a formulation comprising such compounds, its use is contemplated to be within the scope of this invention.

For the production of solid dosage forms, including hard and soft capsules, the therapeutic agent may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further provides controlled-release, sustained-release, or extended-release therapeutic dosage forms for the pharmaceutical composition, in which the composition is incorporated into a delivery system. This dosage form controls release of the active agent(s) in such a manner that an effective concentration of the active agent(s) in the bloodstream can be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent.

In the pharmaceutical compositions of the invention, the active agent(s) may be present in an amount of at least 0.5 and generally not more than 95% by weight, based on the total weight of the composition, including carrier medium and/or supplemental active agent(s), if any. Preferably, the proportion of active agent(s) varies between 30-90% by weight of the composition.

The synthesis, formulation of pharmaceutical compositions, preparation of suitable dose forms, mode and amounts of administration of such dopamine reuptake inhibitors are described in detail in U.S. Patent Application Publication No. US 2009/0215839.

A compound that has been tested for use in the method of the invention is 3-(phenylpropyl)-sydnonimine-N-phenylcarbamoyl, as shown in the following examples. Additional compounds that are also dopamine reuptake inhibitors and may be utilized in the present method include: 3-(p-methylbenzyl)-sydnonimine-N-phenylcarbamoyl, 3-(p-carboxybenzyl)-sydnonimine-N-phenylcarbamoyl, 3-phenethyl-sydnonimine-N-phenylcarbamoyl, 3-phenethyl-sydnonimine-N-(3',4'-dichloro-phenyl)-carbamoyl, 3-(p-nitrophenethyl)-sydnonimine-N-(3',4'-dinitro-phenyl)-carbamoyl, 3-(p-fluorobenzyl)-sydnonimine-N-phenylcarbamoyl, 3-benzyl-sydnonimine-N-phenylcarbamoyl, 3-phenethyl-sydnonimine-N-(p-chlorophenyl)-carbamoyl, 3-phenethyl-sydnonimine-N-(m-trifluoromethyl)-phenylcarbamoyl, 3-(3',5'-difluorobenzyl)-sydnonimine-N-phenylcarbamoyl, 3-(m-fluorobenzyp-sydnonimine-N-phenylcarbamoyl, 3-(p-trifluoromethylbenzyl)-sydnonimine-N-phenylcarbamoyl, 3-(p-tert-butylbenzyl)-sydnonimine-N-phenylcarbamoyl, 3-(p-methylbenzyl)-sydnonimine-N-(p'-trifluoromethyl-phenyl) carbamoyl, and 3-(p-methylbenzyl)-sydnonimine-N-(p-dimethylamino-phenyl)carbamoyl.

The methods of the present invention will normally include medical follow-up to determine the therapeutic or prophylactic effect brought about in the patient undergoing treatment with the compound(s) and/or composition(s) described herein.

The studies described below indicate that enhanced central and/or sympathetic dopaminergic activity resulting from inhibiting dopamine reuptake will mediate conditions associated with diabetes.

While not wishing to be confined to any particular theory as to the mechanism of action of dopamine reuptake inhibitors in treating diabetes symptoms and delaying or preventing diabetes-associated pathologic conditions, as described herein, it is believed that the observed attenuation of diabetic manifestations is due to enhancements of dopaminergic transmissions.

After releasing dopamine into the synaptic cleft, the neurotransmitter extracellular concentration is regulated by the reuptake protein (DAT) and by diffusion. A reuptake inhibitor will block dopamine reuptake, consequently extending the neurotransmitter interaction with its receptors and expanding the domain of dopaminergic ligand-receptor interaction. That is, dopamine reuptake inhibition enhances dopamine neurotransmission temporally and spatially in both central and sympathetic nervous systems.

The following examples are provided to describe the invention in further detail. These examples are provided for illustrative purposes only and are not intended to limit the invention in any way.

EXAMPLE 1

Mediation of hyperglycemic conditions—FVB strain of mice were used in this study. In our previous study (unpublished), we noted that the FVB strain provides a broad phenotypic window for most parameters of human diabetic conditions similar to C57Bl/6. For instance, there was a noted weight gain and obesity induced with high and intermediate fat diets. A persistent high fat diet induces relatively robust hyperglycemic conditions and inefficient glucose disposal but with little noted effects on metabolic rate. There is little circadian impact and changes in activity patterns with the high fat diet.

Figure 1:
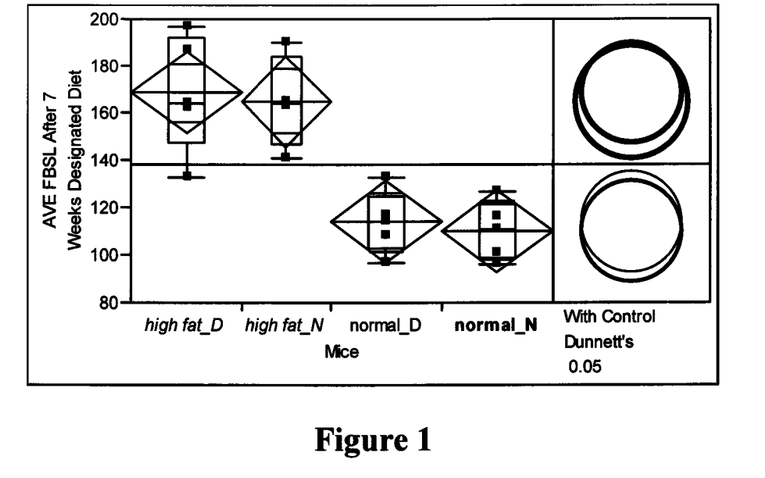
FIG. 1. A graphical representation demonstrating that after seven weeks, mice fed on high fat diet showed robust hyperglycemic condition.

Twenty FVB mice (~12 weeks of age) were randomly separated into two groups (n=10). One group (of ten mice) was fed a high fat diet (ResearchDiets, New Brunswick, N.J., and Cat. #D12492); with the following caloric components: 20 percent protein; 20 percent carbohydrate; and 60 percent fat; 5.24 kcal/gram. Another group was fed with regular rodent chow (Labdiet, Richmond, Ind., product code 5010); 28.7 percent protein, 12.7 percent fat, and 58.6 percent carbohydrate; 3.43 kcal/gram. After seven-weeks, blood glucose levels (and body weight) of the two different groups were examined. As shown in FIG. 1, there was a clear distinction between the blood glucose levels (Comparisons with normal chow control using Dunnett's Method, p=0.0003) between the mice on the high fat diet and normal chow. The group fed on the high fat diet clearly developed a hyperglycemic condition. The difference in body mass was also clearly significant.

Each of the two groups were then further separated into two subgroups (n=5). For the high fat diet group, the separation of the animals from the hyperglycemic/high fat diet group into two sub-groups was normalized based on the blood glucose levels. One group, designated as high fat-D, were treated with a dopamine reuptake inhibitor (3-(phenylpropyl)-sydnonimine-N-phenylcarbamoyl), the other group, designated as high fat-N were treated with vehicle (30% captosol, 1% Tween (Tween® 20, a polyoxyethylene sorbitan esters available from Sigma) and 1% 1N HCl in $H_2O$; hereafter referred to as vehicle). For the normal chow group, the separation was random but similarly designated and separated into drug treated (Normal-D) and vehicle controls (Normal-N). One-way ANOVA analysis of the mean values is shown in FIG. 1. The high fat group remained on the high fat diet; and the Normal Diet group remained on the Normal Diet for the remainder of the study. Within each dietary routine, there were two sub-groups (n=5), i.e. drug treated and placebo/vehicle controls.

On the $8^{th}$ week of the designated dietary routine, both drug-treated groups were given 3-(phenylpropyl)-sydnonimine-N-phenylcarbamoyl at 10 mg/kg (p.o.), whereas the control groups were given an equal volume of vehicle. To avoid any disturbance of circadian rhythm, the drug (or vehicle) administrations were carried out daily at approximately 5 pm six days a week.

Figure 2:
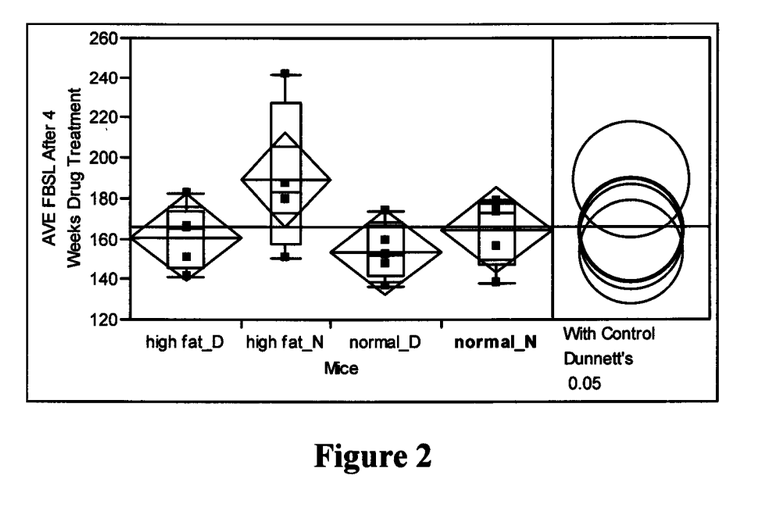
FIG. 2. A graphical representation demonstrating that after 4 weeks of treatment with a dopamine reuptake inhibitor, the blood glucose levels of the dopamine reuptake inhibitor (3-(phenylpropyl)-sydnonimine-N-phenylcarbamoyl) treated mice became indistinguishable from the group of mice fed a Normal Diet.

After 4-weeks of treatment, the blood glucose levels of the mice in different groups and their body mass were again examined. Notably, the body mass of the groups that were on the high fat diet was still noticeably higher than the groups on the Normal Diet regardless of the drug exposure. The results of the blood glucose levels are different. All drug treated groups showed lower levels of blood glucose than their respective sham treated groups; more importantly, there were no discernable differences between the groups that were fed with high fat diet—drug treated and the group that was on Normal Diet with vehicle treatment. A statistical analysis of the different groups is shown in FIG. 2.

EXAMPLE 2

Home-cage health and behavior—This is not a qualitative measurement but the behavior pattern that we noticed during the study. All 4 groups of animals were housed in pairs or trios according to stratification of either treated with drug or vehicle. For three of the 4 groups, e.g. Normal Diet-drug-treated, Normal Diet-vehicle-treated, and high-fat-diet-drug-treated, the animals appear to be healthy, were docile to handlers and non-aggressive with each other. However the high-fat-diet-vehicle-treated group started to develop under-belly lesions, bite marks, and aggressive behavior towards littermates. This pattern of behavior became especially noticeable after overnight fasting (in order for fasting blood glucose level). In fact, after the above mentioned second examination (examination of fasting blood glucose level after 4 weeks of drug treatment), one of the mice in the high-fat-diet-vehicle-treated group had to be euthanized due to wounds and lesions. The remainders (of the four mice) were subsequently housed individually. These changes of behavior patterns and or behavior oddities are likely indicative of neurological changes under pre-diabetic or diabetic conditions. In contrast to the high-fat-diet-vehicle-treated group, the mice in the corresponding group that were treated with the dopamine reuptake inhibitor 3-(phenylpropyl)-sydnonimine-N-phenylcarbamoyl remained healthy, docile and playful with littermates.

EXAMPLE 3

Mediation of diabetic-induced hypoalgesia (Hot-plate assay)—Mice were brought to the testing room and acclimatized for an hour before test. Pain reflexes in response to a thermal stimulus are measured using a Hot Plate Analgesia Meter from Harvard Apparatus. The plate surface was maintained at 48° C. that was measured by a built-in digital thermometer. Mice were placed on the hot plate which is surrounded by a clear acrylic cage with the Start/Stop trigger on the timer. Latencies to respond indicated by shaking or licking or flicking a hind paw were observed (If a mouse does not respond within 120 seconds, the test is terminated and the mouse is removed from the hot plate) and recorded. For each subject, the test was performed three times with about 30 minute rest between tests. Animals were tested one at a time and were not habituated to the apparatus prior to testing.

The results were analyzed by Wilcoxon rank-sum testing, as shown in Table 1

TABLE 1

Wilcoxon/Kruskal-Wallis Tests (Rank Sums)

| Level | Count | Score Sum | Score Mean | (Mean − Mean$^0$)/Std$^0$ |
|---|---|---|---|---|
| High Fat-D | 5 | 33.000 | 6.600 | −1.528 |
| High Fat-N | 4 | 41.000 | 10.250 | 0.050 |
| Normal-D | 5 | 71.000 | 14.200 | 1.898 |
| Normal-N | 5 | 45.000 | 9.000 | −0.417 |

The results indicate that dopamine reuptake inhibition mediates the hypoalgesic (reduced pain sensation by thermal stimulation) conditions induced by diabetic conditions.

EXAMPLE 4

Mediation of diabetic hypoalgesia (Tail-flick assay)—Mice were brought to the testing room, acclimatized and administered 3-(phenylpropyl)-sydnonimine-N-phenylcarbamoyl (5.0 mg/kg; p.o.) an hour before test. Pain reflexes in response to a thermal stimulus are measured using a tail-flick analgesic meter with a built in stop-timer from Columbus Instruments. Latencies to respond for the thermal stimulation is recorder. For each subject, the test was performed three times with about 30 minute rests between tests. Animals are tested one at a time and are not habituated to the apparatus prior to testing.

The results were analyzed by Wilcoxon rank-sum testing, as shown in Table 2.

TABLE 2

Wilcoxon/Kruskal-Wallis Tests (Rank Sums)

| Level | Count | Score Sum | Score Mean | (Mean − Mean$^0$)/Std$^0$ |
|---|---|---|---|---|
| High Fat-D | 5 | 25.000 | 5.000 | −2.268 |
| High Fat-N | 4 | 60.000 | 15.000 | 1.950 |
| Normal-D | 5 | 48.000 | 9.600 | −0.139 |
| Normal-N | 5 | 57.000 | 11.400 | 0.602 |

The results indicate that dopamine reuptake inhibition mediates the hypoalgesic (reduced pain sensation by thermal stimulation) conditions induced by diabetic conditions.

Figure 3:
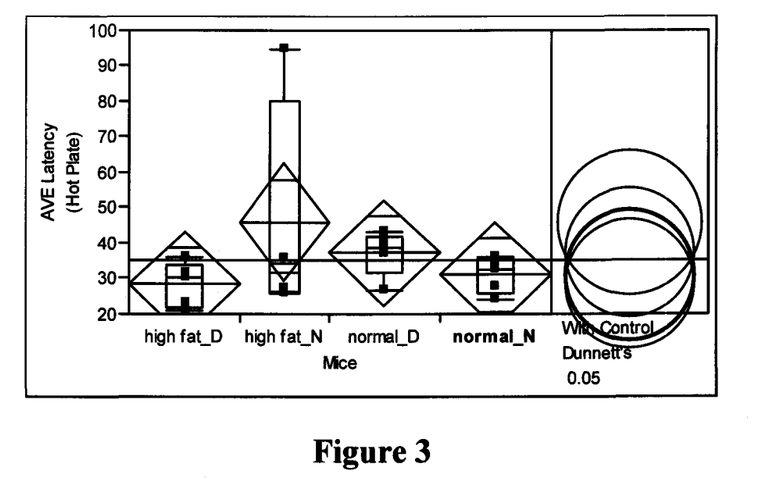
FIG. 3. A graphical representation demonstrating that a dopamine reuptake inhibitor attenuated the hypoalgesic (an indication that recapitulates the human condition of DPN) conditions induced by diabetic conditions (hot plate test).
Figure 4:
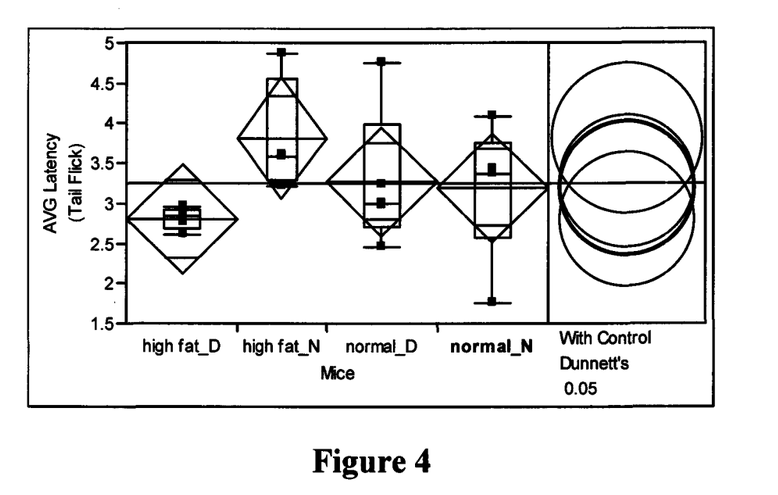
FIG. 4. A graphical representation demonstrating that a dopamine reuptake inhibitor attenuated the hypoalgesic (an indication that recapitulates the human condition of DPN) conditions induced by diabetic conditions (tail-flick test).

With different testing methods and drug administration routines, the comparative results between different groups of mice have been consistent. As shown in FIGS. 3 and 4, there is a significant increase in latency responding to thermal stimulation with the group treated with vehicle, fed on the high fat diet, and which showed signs of hyperglycemia and aggressive (unstressed) behavior. In other words, the group of mice that has been on the high fat diet without drug treatment developed hypoalgesia. In fact, this is the group of mice that developed phenotypic diabetic manifestations recapitulating many aspects of the human diabetic symptoms.

Equally noteworthy is the comparison of the thermal responses between the high-fat-diet-drug-treated subjects (which otherwise would have developed hypoalgesia without drug intervention) and the Normal Diet-vehicle-treated (supposedly with Normal-Nociceptive threshold). Between these two groups, virtually no difference was observed, indicating that enhanced dopaminergic neurotransmission by the reuptake inhibitor mediated sensory neuropathy. In human this implication may indicate the attenuation or mediation of the loss of distal sensation due to diabetic neuropathy.

A number of patent documents and non-patent documents are cited in the foregoing specification in order to describe the state of the art to which this invention pertains. The entire disclosure of each of the cited documents is incorporated by reference herein.

While various embodiments of the present invention have been described and/or exemplified above, numerous other embodiments will be apparent to those skilled in the art upon review of the foregoing disclosure. The present invention is, therefore, not limited to the particular embodiments described and/or exemplified, but is capable of considerable variation and modification without departure from the scope of the appended claims. Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention.

LIST OF REFERENCES

1. Blum, K., Chen, A. L. C., Braverman, E. R., Comings, D. E., Chen, T. J. H., Arcuri, V., Blum, S., Downs, B. W., Waite, R. L., Notaro, A., Lubar, J., Williams, L., Prihoda, T. J., Palomo, T., and Oscar-Berman, M. Attention-deficit-hyperactivity disorder and reward deficiency syndrome, *Neuropsychiatric Disease and Treatment*, 4:893-917 (2008).
2. Campbell, B. C. and Eisenberg, D., Obesity, Attention Deficit-Hyperactivity Disorder and the Dopaminergic Reward System, *Coll. Antropol.*, 1:33-8 (2007).
3. Gallego, M., Setiéen, Izquiero, M. J., Casis, O., and Casis, E. Diabetes-Induced Biochemical Changes in Central and Peripheral Catecholaminergic Systems, *Phsiol. Res.*, 52:735-41 (2003).
4. Morrison, J. F. B., Shehab, S., Sheen, R., Dhanasekeran, S., Shaffiullah, M., and Mensah-Brown, E. Sensory and autonomic nerve changes in the monosodium glutamate-treated rat: a model of type II diabetes. *Exp Physiol*, 93:213-22 (2007).
5. Ramakrishan, R., Kempuraj, D., Prabhakaran, K., Jayakumar, A. R., Devi, R. S., Suthanthirarajan, N., and Namasivayam, A. A short-term diabetes induced changes of catecholamines and p38-MAPK in discrete areas of rat brain. *Life Sciences*, 77:1825-35 (2005).
6. Russell, V. A., Oades, R. D., Tannock, R., Killeen, P. R., Auerbach, J. G., Johansen, E. B., and Sagvolden, T. Response variability in Attention-Deficit/Hyperactivity Disorder: a neuronal and glial energetics hypothesis. *Behavioral and Brain Functions*, 2:30 (2006).
7. United States Patent Pub. No. US2009/0215839.

What is claimed is:

1. A method for treatment of symptoms of Type II diabetes and delay of onset or occurrence of pathologic conditions associated with Type II diabetes in a patient in need thereof wherein said diabetes-associated pathologic conditions comprise at least one selected from the group of diabetic sensory neuropathy, diabetic autonomic neuropathy, diabetic retinopathy, diabetic nephropathy and diabetic angiopathy, said method consisting essentially of administering an amount of a dopamine reuptake inhibitor that is effective for said treatment and said delay, the dopamine reuptake inhibitor is a compound selected from the group consisting of 3-(phenylpropyl)-sydnonimine-N-phenylcarbamoyl, 3-(p-methylbenzyl)-sydnonimine-N-phenylcarbamoyl, 3-(p-carboxybenzyl)-sydnonimine-N-phenylcarbamoyl, 3-(p-fluorobenzyl)-sydnonimine-N-phenylcarbamoyl, 3-(3',5'-difluorobenzyl)-sydnonimine-N-phenylcarbamoyl, 3-(m-fluorobenzyl)-sydnonimine-N-phenylcarbamoyl, 3-(p-trifluoromethylbenzyl)-sydnonimine-N-phenylcarbamoyl, 3-(p-tert-butylbenzyb-sydnonimine-N-phenylcarbamoyl, 3-(p-methylbenzyl)-sydnonimine-N-(p'-trifluoromethyl-phenyl)carbamoyl, and 3-(p-methylbenzyl)-sydnonimine-N-(p-dimethylamino-phenyl)carbamoyl, and the pharmaceutically acceptable salts of said compound.

2. The method of claim 1, wherein said diabetic symptoms are symptoms of a pre-diabetic condition.

3. The method of claim 1, wherein said diabetic symptoms include at least hyperglycemia.

4. The method of claim 1, wherein said patient is a mammal.

5. The method of claim 1, wherein said patient is a human.

6. The method of claim 1, wherein said dopamine reuptake inhibitor is formulated with a pharmaceutically acceptable carrier medium for administration to said patient.

7. The method of claim 1, wherein said dopamine reuptake inhibitor is administered via a route of administration selected from the group of oral, parenteral, intravenal, intraarterial infusion, intramuscular, intraperitoneal, intrathecal, subcutaneous injection, liposome-mediated delivery, rectally, vaginally, inhalation, insufflation, transdermally or otic delivery.

8. The method of claim 1, wherein said dopamine reuptake inhibitor is 3-(phenylpropyl)-sydnonimine-N-phenylcarbamoyl, or a pharmaceutically acceptable salt thereof.

* * * * *